(12) United States Patent
Houser et al.

(10) Patent No.: US 6,423,082 B1
(45) Date of Patent: Jul. 23, 2002

(54) ULTRASONIC SURGICAL BLADE WITH IMPROVED CUTTING AND COAGULATION FEATURES

(75) Inventors: Kevin L. Houser, Springboro; Jorge N. Gutierrez, Cincinnati; Sarah A. Cook, Cincinnati; Laura A. Gallagher, Cincinnati, all of OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 09/540,620

(22) Filed: Mar. 31, 2000

(51) Int. Cl.[7] .............................................. A61B 17/32
(52) U.S. Cl. ..................................................... 606/169
(58) Field of Search ...................... 606/99, 169; 604/22; 601/2

(56) References Cited

U.S. PATENT DOCUMENTS

| | | | |
|---|---|---|---|
| 5,167,725 A | | 12/1992 | Clark et al. |
| 5,263,957 A | | 11/1993 | Davison |
| 5,318,570 A | * | 6/1994 | Hood et al. ................... 606/169 |
| 5,322,055 A | | 6/1994 | Davison et al. |
| 5,324,299 A | | 6/1994 | Davison et al. |
| 5,810,859 A | | 9/1998 | DiMatteo et al. |

FOREIGN PATENT DOCUMENTS

| | | |
|---|---|---|
| EP | 0 456 470 al | 11/1991 |
| EP | 0 830 845 | 3/1998 |
| EP | 0 970 659 A1 | 12/2000 |

* cited by examiner

Primary Examiner—Eduardo C. Robert
(74) Attorney, Agent, or Firm—Verne E. Kreger

(57) ABSTRACT

The present invention is directed to an ultrasonic surgical blade including a top surface, a bottom surface and a cutting-edge. The cutting-edge is defined by a cutting-surface intermediate the top surface and the bottom surface, and the top surface has a width greater than the width of the bottom surface. The blade may be straight or curved. In one embodiment of the invention, at least a portion of the cutting-surface is substantially parallel to at least a portion of the top surface. In still another embodiment of the invention first and second side-walls intersect the top surface to form first and second cutting-edges that may be sharp or blunt. Alternately, a second cutting-edge may be defined by a second cutting surface intermediate the top and bottom surfaces. Depending on the angle between the intermediate cutting-surface and the top surface, the cutting-edge may be sharp or blunt. In yet another embodiment of the present invention, a central ridge is provided on the bottom surface of the blade to eliminate blade burrowing and improve precision during coagulation. The cutting-edge is optimized to increase cutting speed of the blade while providing desirable hemostasis. The invention is of particular benefit for breast surgery, due to its cutting and coagulation characteristics.

24 Claims, 10 Drawing Sheets

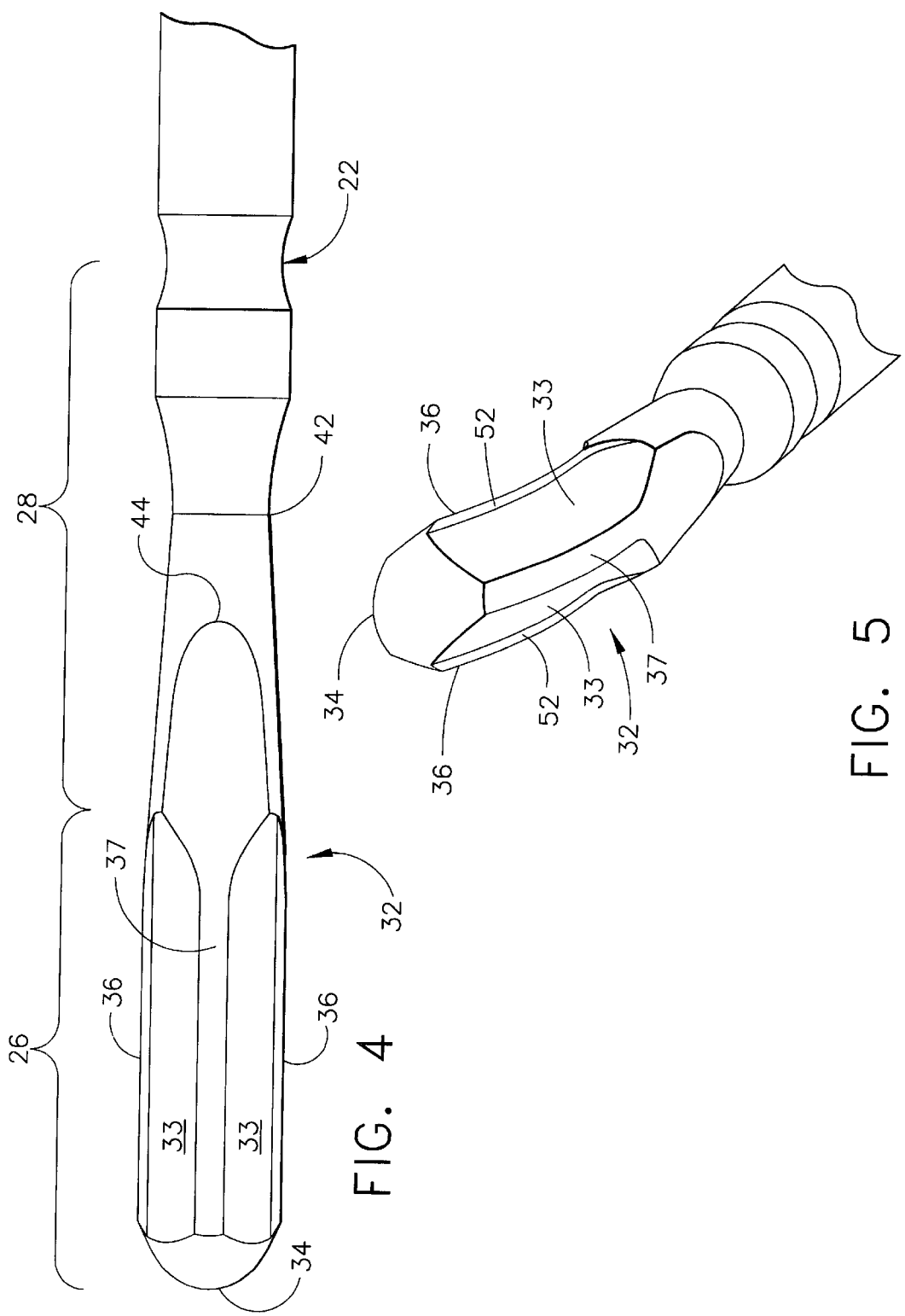

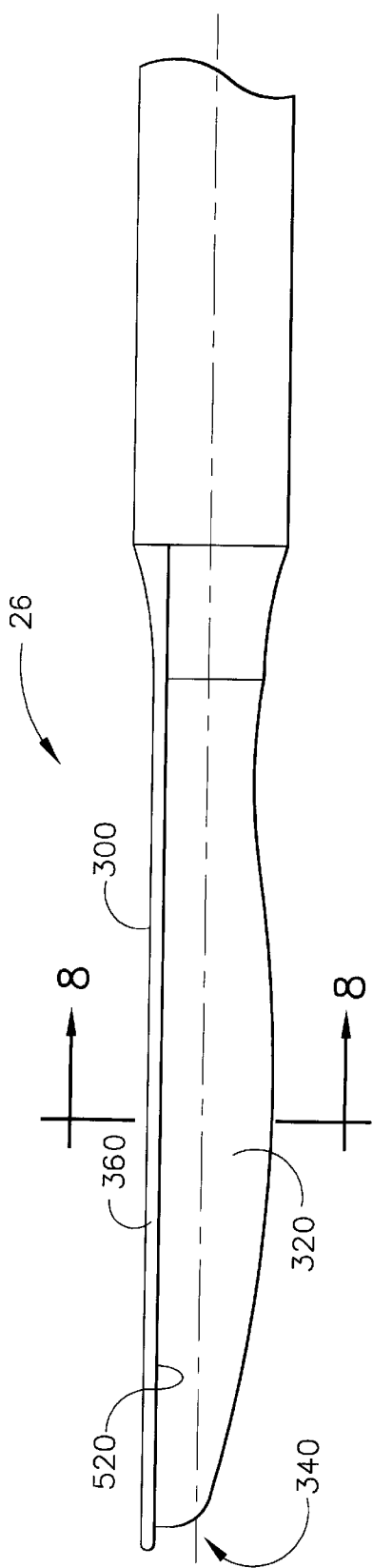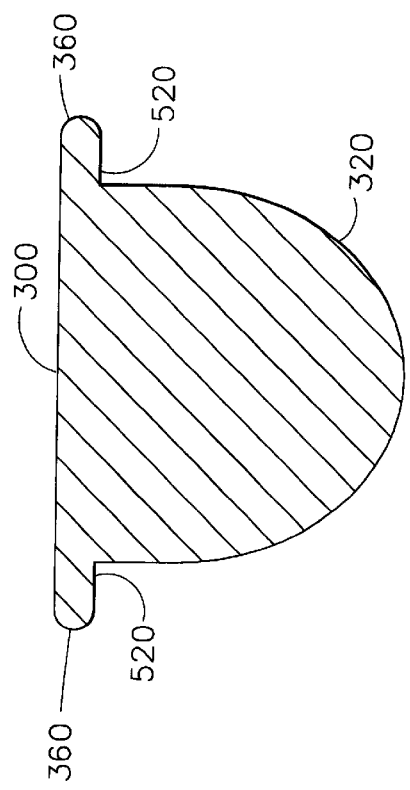
FIG. 7
FIG. 8

US 6,423,082 B1

ULTRASONIC SURGICAL BLADE WITH IMPROVED CUTTING AND COAGULATION FEATURES

This application is related to the following patent applications: application Ser. No. 09/106,415 filed Jun. 29, 1999; now U.S. Pat. No. 6,309,400 application Ser. No. 09/413,225 filed Oct. 5, 1999; and application Ser. No. 09/541,371 filed Mar. 31, 2000.

FIELD OF THE INVENTION

The present invention relates, in general, to ultrasonic surgical blades for use in surgical instruments and, more particularly, to an ultrasonic surgical blade with improved cutting and coagulation features.

BACKGROUND OF THE INVENTION

Ultrasonic instruments, including both hollow core and solid core instruments, are used for the safe and effective treatment of many medical conditions. Ultrasonic instruments, and particularly solid core ultrasonic instruments, are advantageous because they may be used to cut and/or coagulate organic tissue using energy in the form of mechanical vibrations transmitted to a surgical end-effector at ultrasonic frequencies. Ultrasonic vibrations, when transmitted to organic tissue at suitable energy levels and using a suitable end-effector, may be used to cut, dissect, or cauterize tissue. Ultrasonic instruments utilizing solid core technology are particularly advantageous because of the amount of ultrasonic energy that may be transmitted from the ultrasonic transducer, through the waveguide, to the surgical end-effector. Such instruments may be used for open procedures or minimally invasive procedures, such as endoscopic or laparoscopic procedures, wherein the end-effector is passed through a trocar to reach the surgical site.

Activating the end-effector (e.g. cutting blade) of such instruments at ultrasonic frequencies induces longitudinal vibratory movement that generates localized heat within adjacent tissue, facilitating both cutting and coagulation. Because of the nature of ultrasonic instruments, a particular ultrasonically actuated end-effector may be designed to perform numerous functions, including, for example, cutting and coagulation. The structural stress induced in such end-effectors by vibrating the blade at ultrasonic frequencies may have a number of undesirable effects. Such undesirable effects may include, for example, transverse motion in the instrument waveguide that may lead to, for example, excess heat generation in the waveguide or premature stress failure.

Long thin ultrasonic waveguides, such as those used in instruments for minimally invasive surgery, are particularly susceptible to transverse vibrations introduced by imbalances in the end-effector. For certain applications, it is desirable to include one or more axially asymmetrical features, (e.g. blade curvature) to enhance performance of the end-effector. It may also be desirable to design such end-effectors to be relatively long, in order to facilitate certain surgical procedures. A method of balancing asymmetric ultrasonic surgical blades is described in U.S. patent application Ser. No. 09/106,661 filed Jun. 29, 1999, hereby incorporated herein by reference.

Although ultrasonic surgical instruments such as those described in U.S. patent application Ser. No. 09/106,661 have been eminently successful, some areas of improvement still remain. One complaint sometimes heard from surgeons is that cutting is too slow, or that control is not as precise as would be desired. Ultrasonic surgical blade edges are often dulled or rounded to slow the cutting process, thereby providing more heat delivery to the tissue during cutting. This improves hemostasis during cutting. It would, therefore, be desirable to design an improved ultrasonic surgical blade. It would further be advantageous to provide an ultrasonic surgical blade that cuts faster, while maintaining hemostasis desired by the surgeon. It would also be advantageous to provide an ultrasonic surgical blade that is more controllable and precise, to providing cutting where needed with significant control. An ultrasonic surgical instrument is described with improved cutting and coagulation features to provide these advantages and overcome the disadvantages of previous instruments.

SUMMARY OF THE INVENTION

The present invention is directed to an ultrasonic surgical blade including a top surface, a bottom surface and at least one cutting-edge. The cutting-edge is defined by a cutting-surface intermediate the top surface and the bottom surface, and whereby the top surface has a width greater than the width of the bottom surface. The cutting-edge is optimized to increase cutting speed of the blade while providing desirable hemostasis. Further, the blade may be straight or curved. In one embodiment, at least a portion of the cutting-surface is substantially parallel to at least a portion of the top surface. In still a further embodiment, the cutting edge is defined by a second cutting surface that intersects the first cutting surface to form the cutting edge. In yet another embodiment of the invention, the bottom surface further includes a first side-wall that intersects the first cutting-surface to form the first cutting-edge. Depending on the angle between the cutting-surfaces and the top surface, the cutting-edge may be sharp or blunt. In yet another embodiment of the present invention, a central ridge is provided on the bottom surface of the blade to eliminate blade burrowing and improve precision during coagulation. A second cutting edge may be formed by including a second intermediate cutting surface formed between the top and bottom surfaces. The second cutting edge may be further defined by a second cutting surface intersecting the second intermediate cutting surface and/or a second side wall intersecting the second intermediate cutting surface to form the second cutting edge.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 4 is a bottom view of the distal end of an ultrasonic transmission assembly according to the present invention;

FIG. 5 is a bottom perspective view of the distal end of an ultrasonic transmission assembly according to the present invention;

FIG. 7 is a side view of a straight blade in accordance with the present invention;

FIG. 8 is a section view taken along line 8—8 of FIG. 7;

FIG. 10-A is an alternate embodiment section view taken along line 10—10 of FIG. 9;

DETAILED DESCRIPTION OF THE INVENTION

The present invention relates, in general, to ultrasonic surgical blades for use in surgical instruments and, more particularly, to an ultrasonic surgical blade with improved cutting and coagulation features. A blade according to the present invention is of particular benefit for breast surgery, due to its cutting and coagulation characteristics, however the blade is useful for general soft tissue cutting and coagulation. The blade may be straight or curved, and useful for both open or laparoscopic applications.

Figure 1:
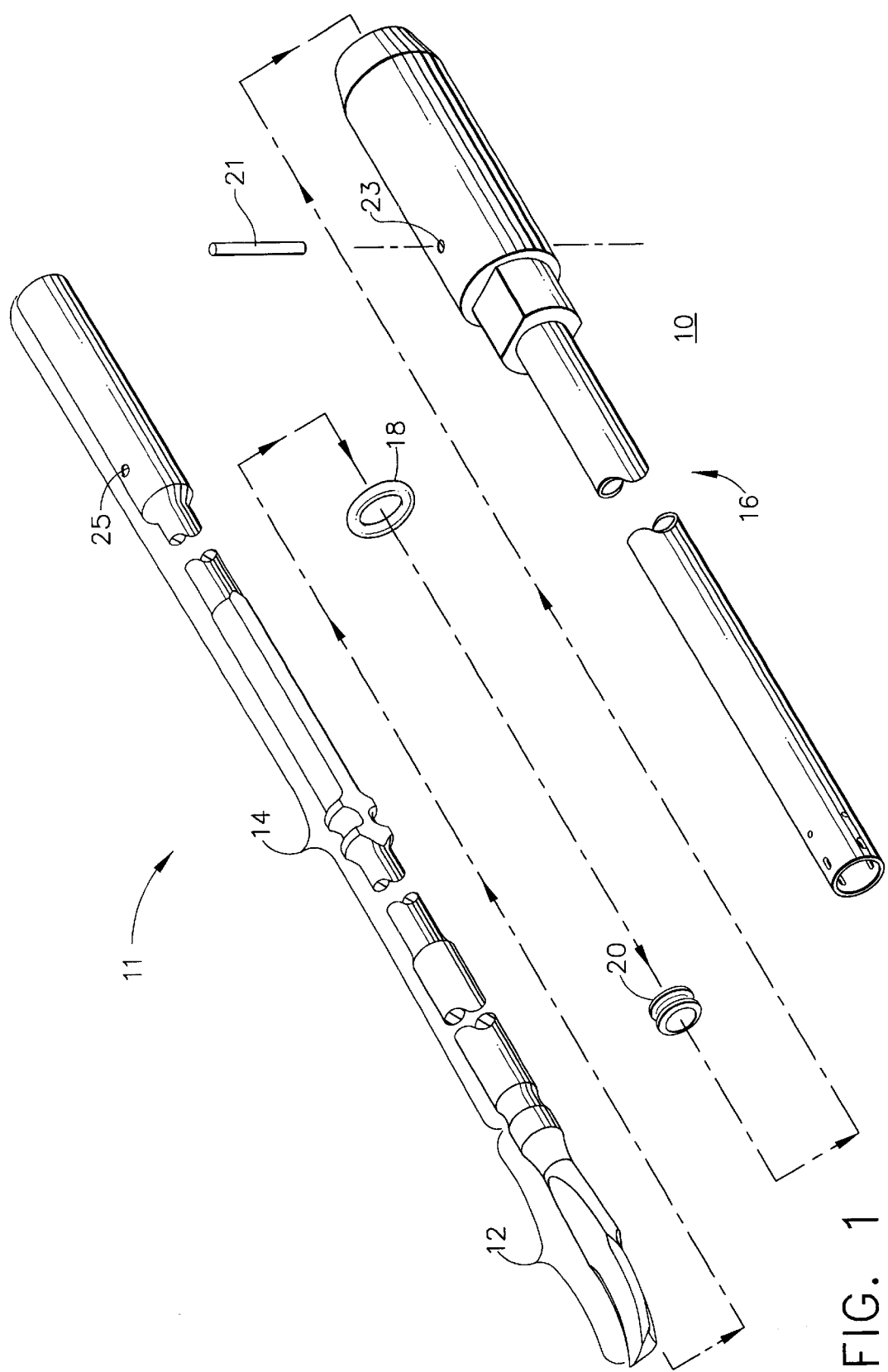
FIG. 1 is an exploded perspective view of an ultrasonic surgical instrument according to the present invention.

FIG. 1 illustrates an exploded perspective view of a sterile ultrasonic surgical instrument 10 according to the present invention. Ultrasonic surgical instrument 10 may be sterilized by methods known in the art such as, for example, gamma radiation sterilization, Ethelyne Oxide processes, autoclaving, soaking in sterilization liquid, or other known processes. In FIG. 1, ultrasonic transmission assembly 11 includes an ultrasonic end-effector, generally designated blade 12, and ultrasonic transmission waveguide 14. Ultrasonic blade 12 and ultrasonic transmission waveguide 14 are illustrated as a single unit construction from a material suitable for transmission of ultrasonic energy such as, for example, Ti6Al4V (an alloy of Titanium including Aluminum and Vanadium), Aluminum, Stainless Steel, or other known materials. Alternately, blade 12 may be separable (and of differing composition) from waveguide 14, and coupled by, for example, a stud, welding, gluing, or other known methods.

Ultrasonic transmission waveguide 14 is positioned in outer sheath 16 by mounting o-ring 18 and sealing ring 20. One or more additional dampers or support members (not shown) may also be included along ultrasonic transmission waveguide 14. Ultrasonic transmission waveguide 14 is affixed to outer sheath 16 by mounting pin 21, that passes through mounting holes 23 in outer sheath 16 and mounting slot 25 in transmission waveguide 14.

Figure 2:
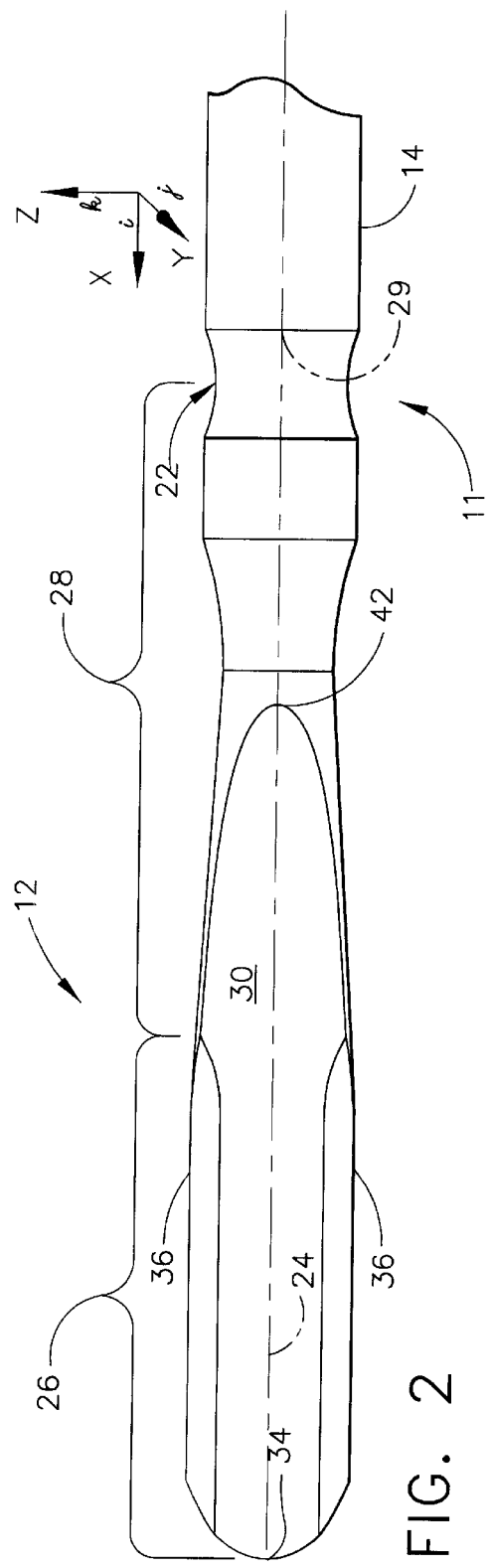
FIG. 2 is a top view of the distal end of an ultrasonic transmission assembly according to the present invention.

FIG. 2 includes an ordinate system in which: the x-axis lies along central axis 24 of ultrasonic transmission waveguide 14 while the y-axis is the axis of curvature of treatment region 26. In the embodiments of the invention described herein, blade 12 is affixed to the distal end of transmission waveguide 14 at balance node 22. Central axis 24 of transmission waveguide 14 extends from the proximal end of transmission waveguide 14 to the distal end of transmission waveguide 14. Blade 12 includes treatment region 26, located at the distal end of blade 12. Treatment region 26 further includes rounded tip 34.

Figure 3:
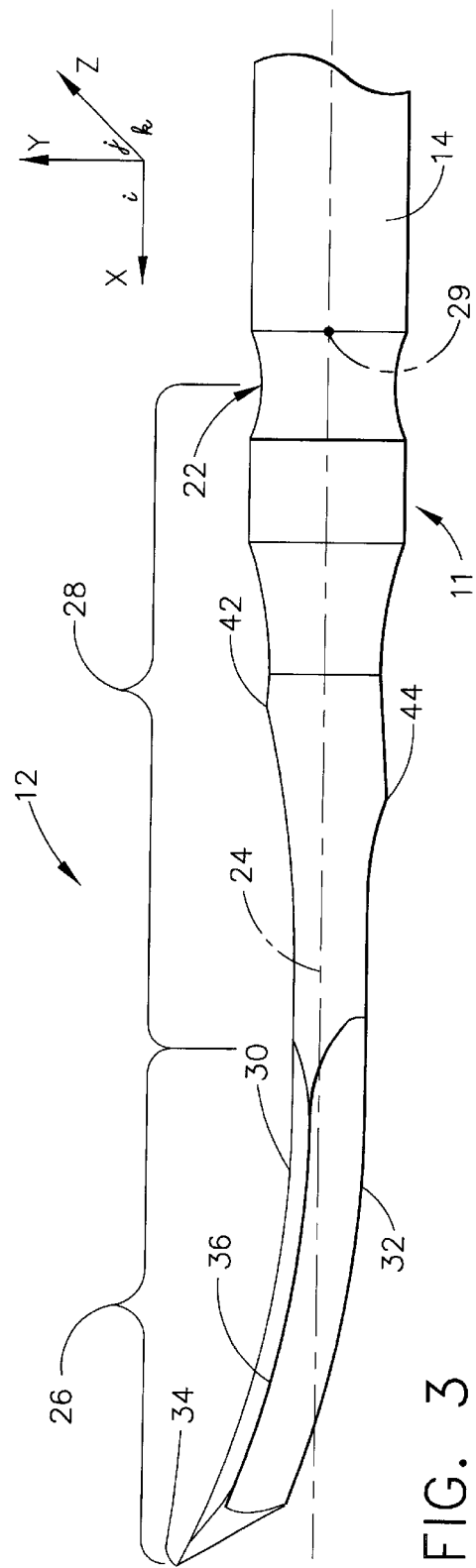
FIG. 3 is a side view of the distal end of an ultrasonic transmission assembly according to the present invention.
Figure 6:
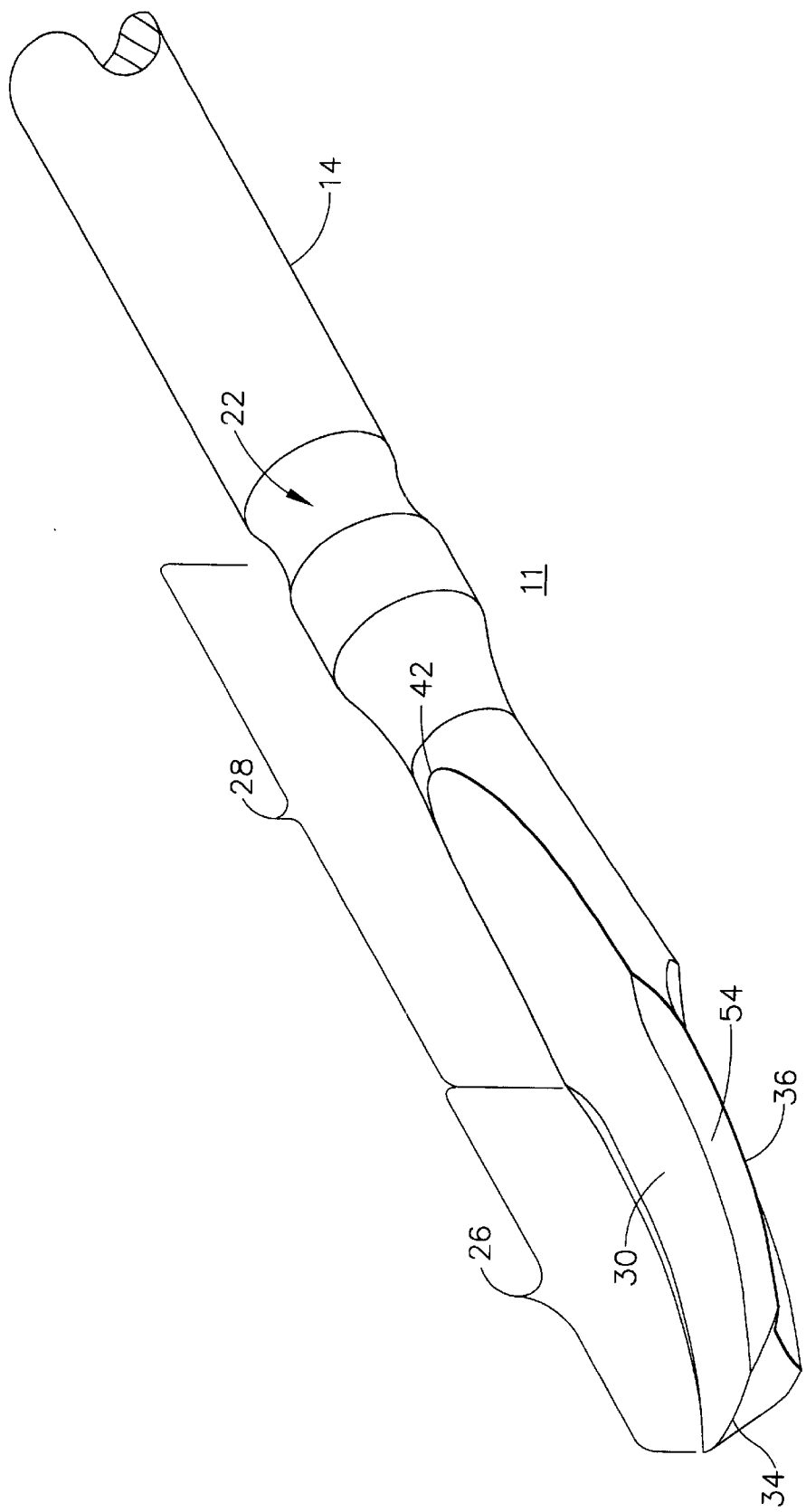
FIG. 6 is a top perspective view of the distal end of the ultrasonic transmission assembly shown in FIG. 5.

Referring to FIG. 3, treatment region 26 includes one or more cutting-edges 36. Cutting-edges 36 (only one shown) are positioned on both sides of treatment region 26 and extend from the proximal end of treatment region 26 to rounded tip 34. Treatment region 26 includes atop surface 30 and a bottom surface 32. Top surface 30 is substantially planar or flat along the z-axis of the blade.

As illustrated in FIG. 4, bottom surface 32 includes side-walls 33 and central ridge 37. Central ridge 37 runs from the distal end of balance region 28 to rounded tip 34 along the center of treatment region 26. Central ridge 37 adds strength, stiffness and rigidity to treatment region 26.

Figure 10:
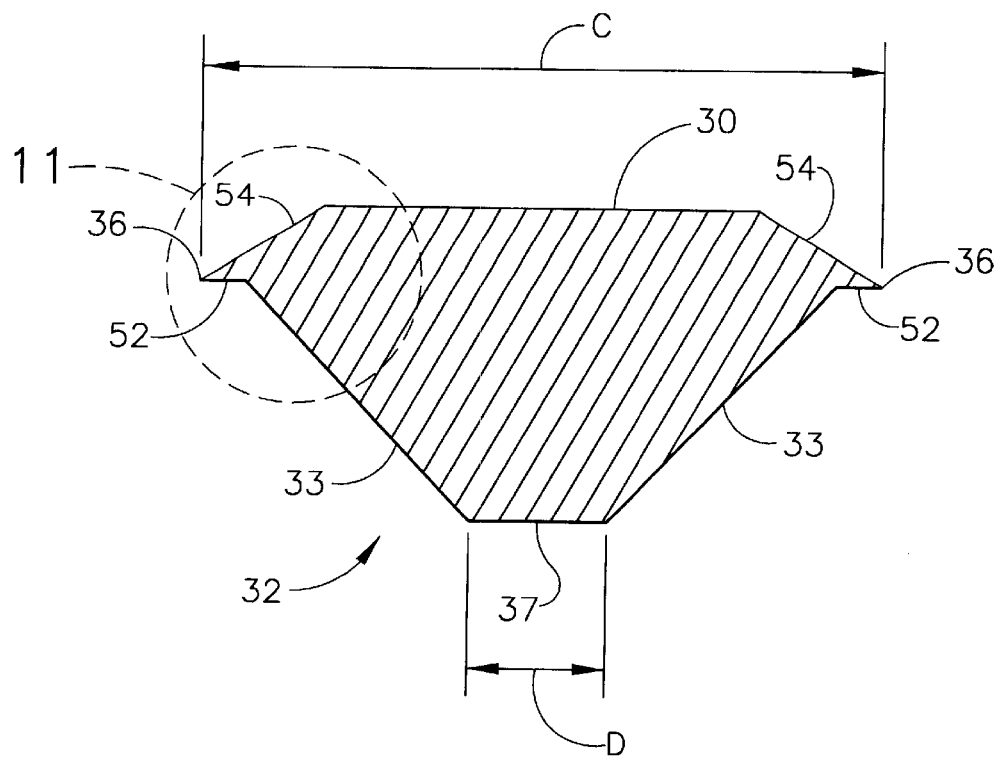
FIG. 10 is a section view taken along line 10—10 of FIG. 9.
Figure 10A:
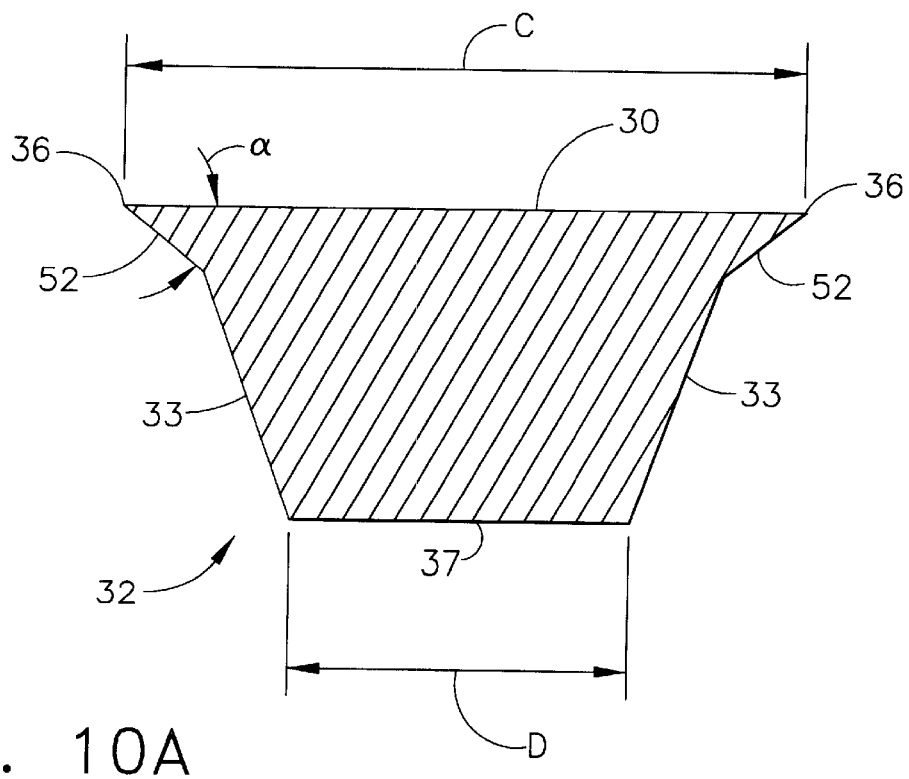

In FIG. 5, central ridge 37 and side-walls 33 form the substantial portion of bottom surface 32. Side-walls 33 originate at central ridge 37 and terminate at cutting-surface 52. Cutting-edge 36 is defined by the intersection of top surface 30 and cutting-surface 52 as shown in FIG. 10-A. Alternatively, top surface 30 may include a second cutting-surface 54, whereby cutting-edge 36 is defined by the intersection of second cutting-surface 54 and cutting-surface 52, as illustrated in FIG. 10.

FIGS. 7 and 8 illustrate an alternate embodiment of the present invention wherein top surface 300 does not include a second cutting-surface. Treatment region 26 includes one or more cutting-edges 360. Cutting-edges 360 are positioned on both sides of treatment region 26 and extend from the proximal end of treatment region 26 to rounded tip 340. Treatment region 26 includes a top surface 300 and a bottom surface 320. Top surface 300 is substantially planar or flat along the z-axis of the blade, but may alternately be curvilinear. Cutting-edge 360 is defined by the intersection of top surface 300 and cutting-surface 520.

Figure 9:
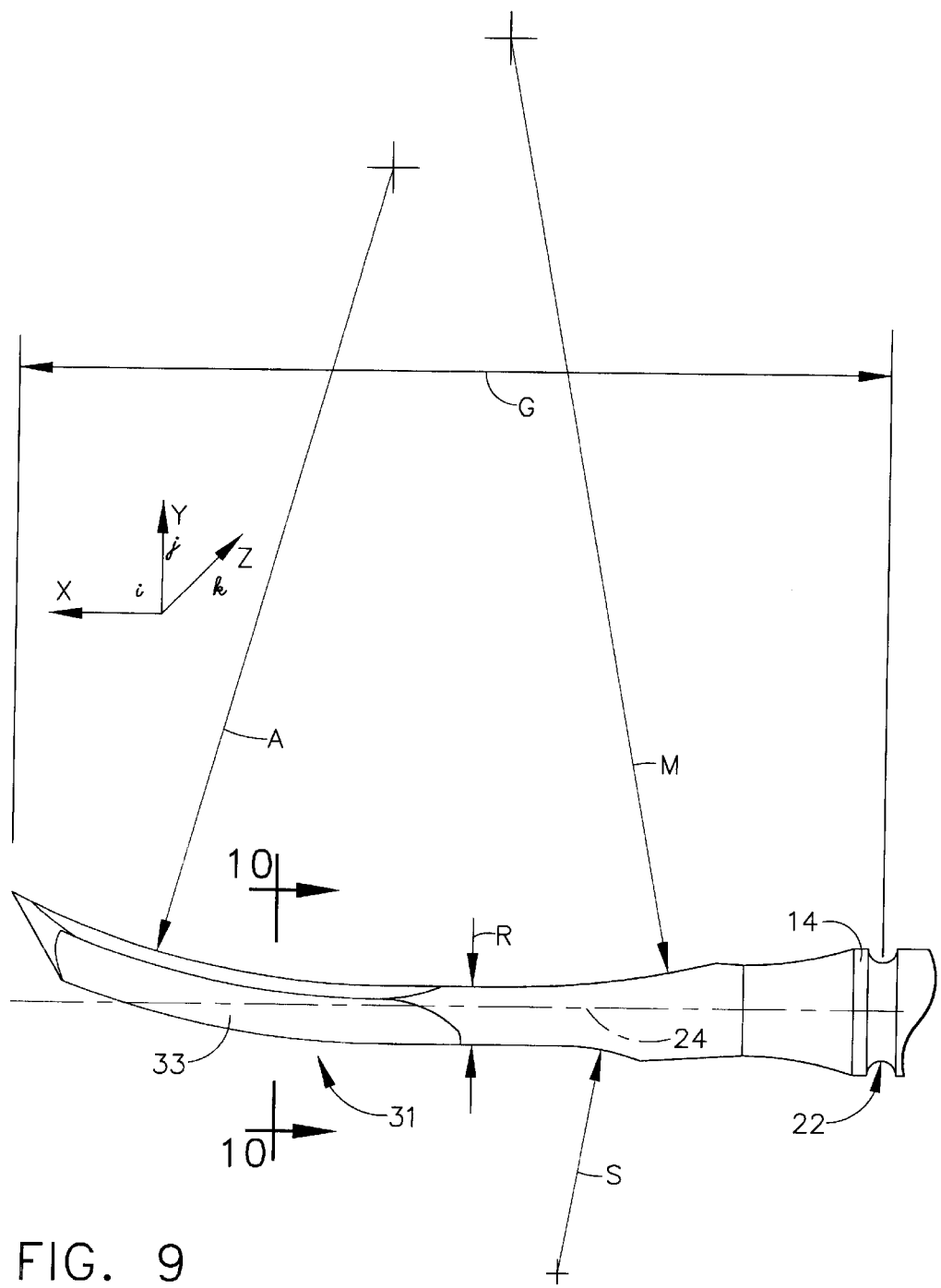
FIG. 9 is a side view of a curved blade according to the present invention, including radii of curvatures.

In FIG. 9, treatment region 26 is a curved blade 31, having a blade curvature A. In one embodiment of the present invention, blade curvature A may be, for example, about 0.9 inches±about 0.3 inches. Further, curved blade 31 may have a thickness R of about 0.050 inches±about 0.02 inches. Curved blade 31 may, in one embodiment of the invention, include first radius of curvature M and second radius of curvature S. In this embodiment of the invention, first radius of curvature M and second radius of curvature S act as first and second balance features respectively. In one embodiment of the present invention, radius of curvature S may be, for example, about 0.25 inches±about 0.125 inches. In the illustrated embodiment of the invention, curved blade 31 may have a radius M of approximately about 0.750 inches±about 0.749 inches. In one embodiment of the invention, curved blade 31 may have a length G of approximately 1.0 inches±about 0.5 inches where G is measured from node point 22 to the distal end of curved blade 31.

In the embodiment of the invention illustrated in FIG. 10, top surface 30 has a width C of, for example, about 0.115 inches±about 0.001 inches. Central ridge 37 has a width D of, for example, about 0.030 inches±about 0.003 inches. In the embodiment of FIG. 10, the cross section of curved blade 31 is formed by side-walls 33, central ridge 37, cutting-surface 52, and top surface 30. Top surface 30 has a width about 0.004 inches wider than the width of bottom surface 32, and preferably, about 0.010 inches wider than the width of bottom surface 32.

Figure 11:
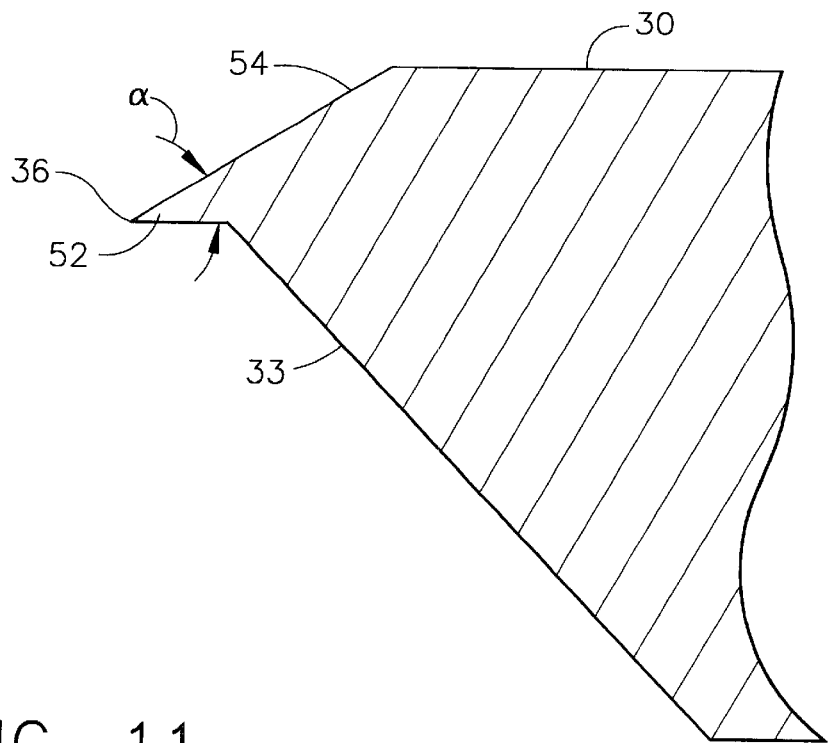
FIG. 11 is a magnification of the blade edge region indicated in FIG. 10.

The cutting-edge 36 is seen in greater detail in FIG. 11. Top surface 30 is beveled, or shaved, by second cutting-surface 54. Second cutting-surface 54 intersects cutting-surface 52 with an included angle of $\alpha$. Angle a has a useful range of from about 10 to about 60 degrees, and is preferably within the range of about 25 to about 35 degrees. The width of cutting-surface 52 has a useful range of from about 0.002 to about 0.060 inches, and is preferably within the range of about 0.005 to about 0.020 inches. Providing cutting-edges 36 with cutting-surface 52 has the unexpected result of increasing the cutting speed of treatment region 26 without compromising coagulation.

Figure 12:
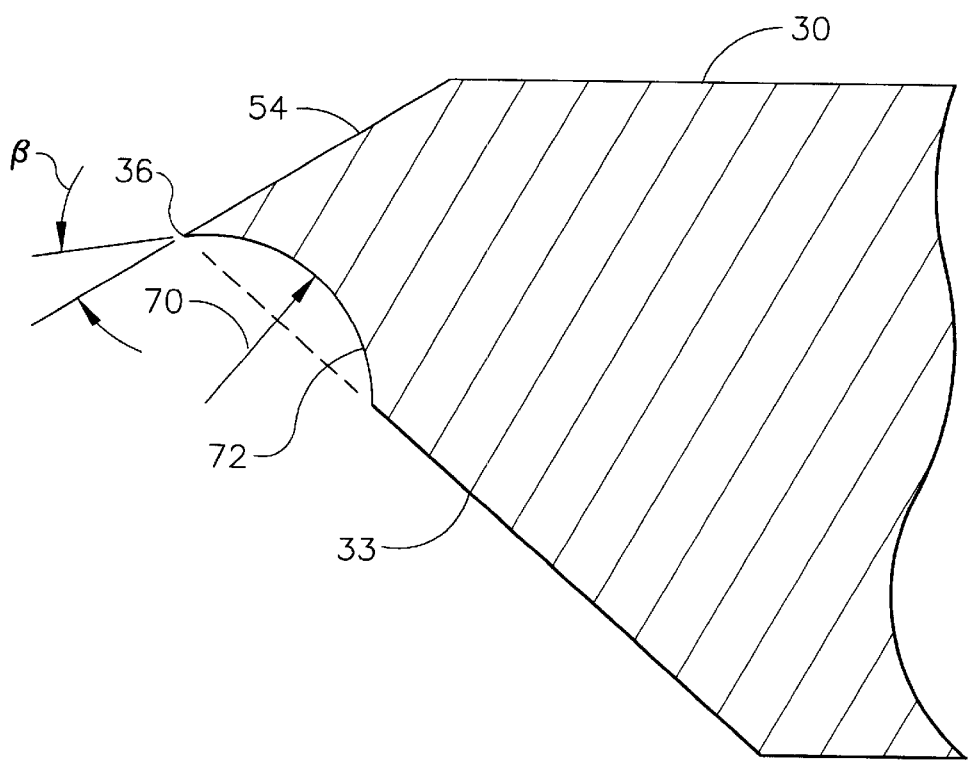
FIG. 12 is a magnification of an alternate embodiment of the blade edge region indicated in FIG. 10.

The embodiment of FIG. 12 illustrates an alternate way to provide a cutting-surface to an ultrasonic blade in accordance with the present invention. In this embodiment, side-wall 33 meets second cutting-surface 54 through radial-cutting-surface 72. Radial cutting-surface 72 may be formed by, for example, machining side-wall 33 with a rounded cutting tool having a radius of curvature 70. Angle β is the angle between the tangent of radial-cutting-surface 72 at edge 36 and second cutting-surface 54. Angle β has a useful range of from about 10 to about 60 degrees, and is preferably within the range of about 25 to about 35 degrees.

Figure 13:
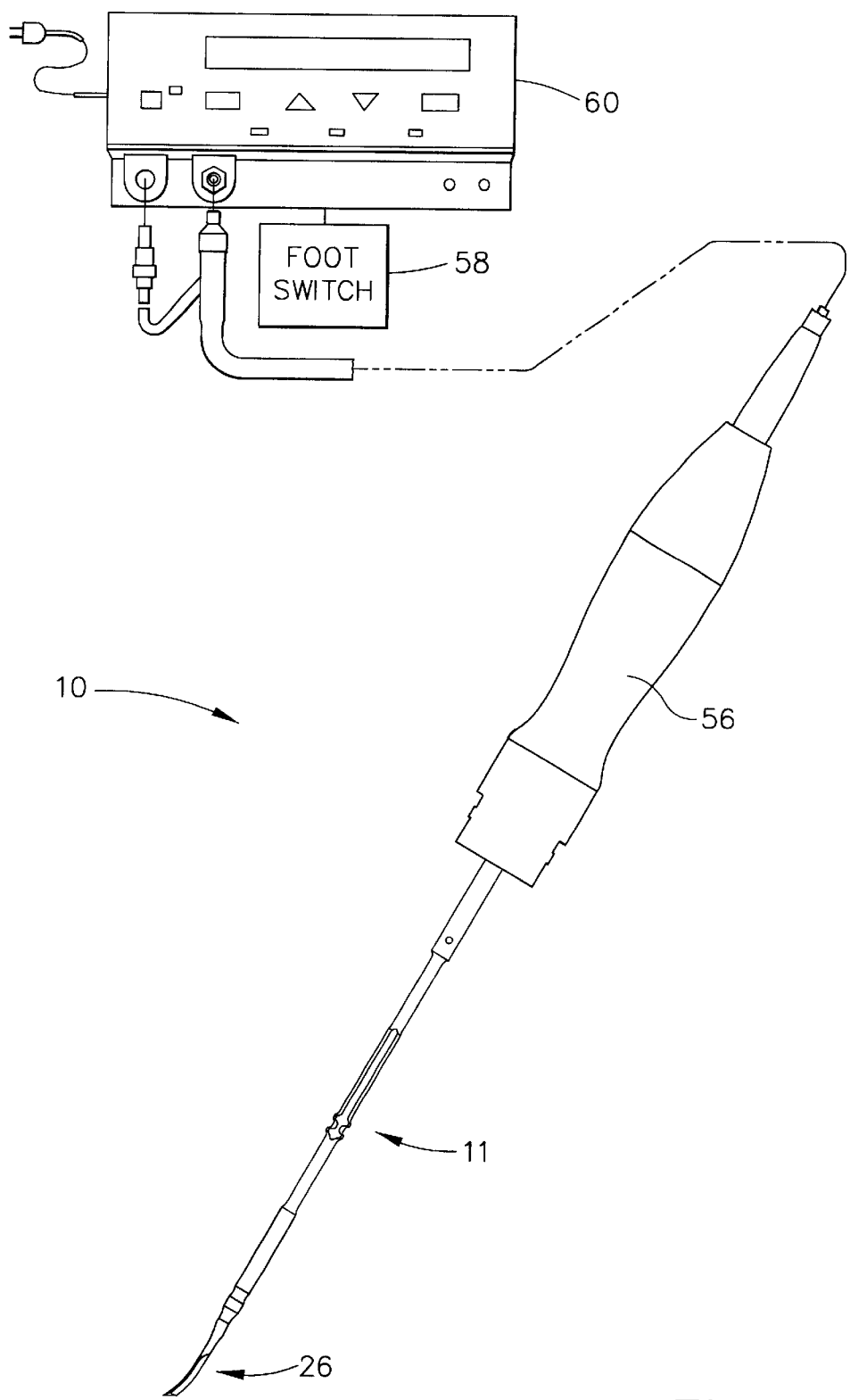
FIG. 13 illustrates a blade in accordance with the present invention connected to an ultrasonic transducer and its associated ultrasonic generator.
Figure 14:
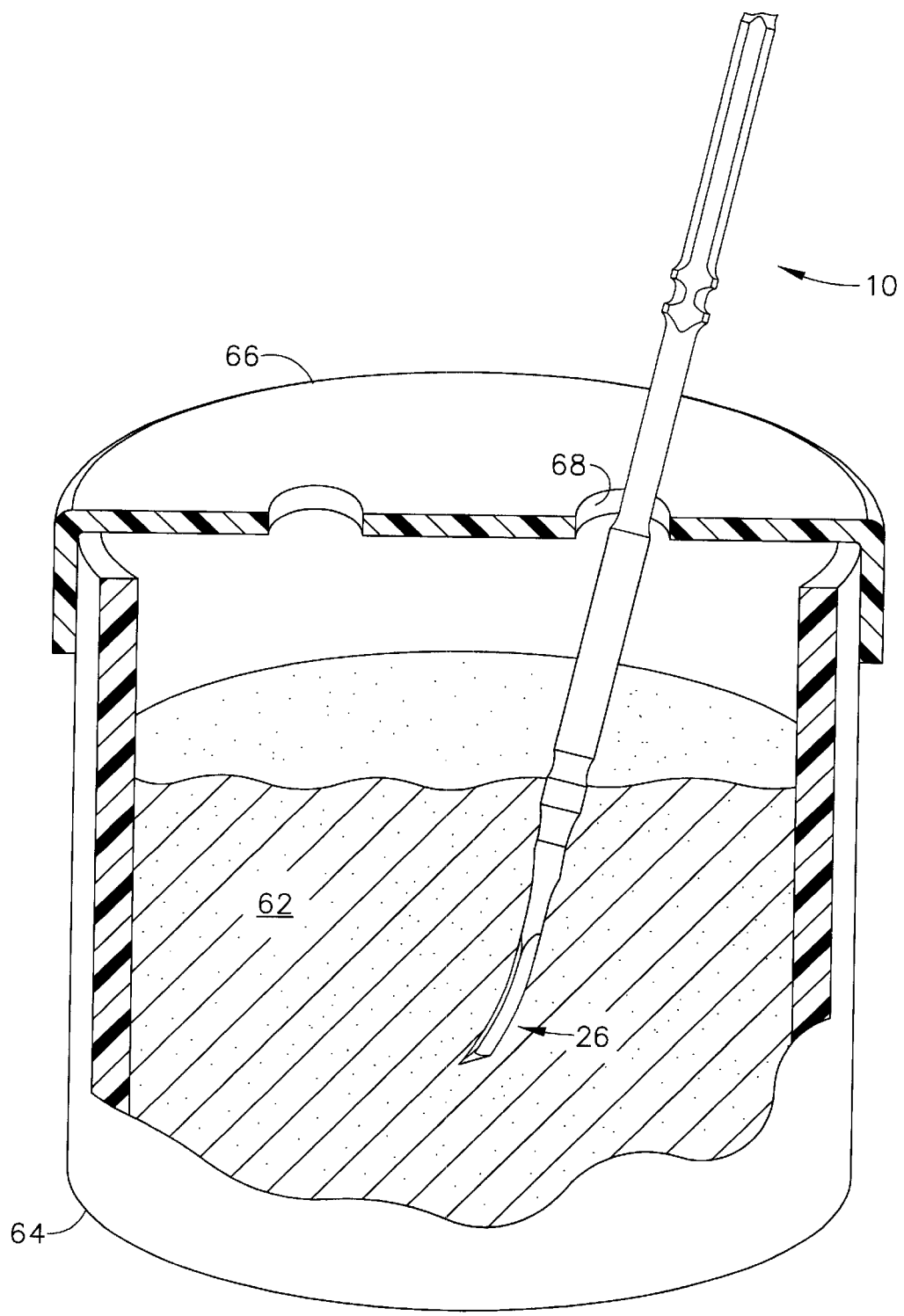
FIG. 14 illustrates a method of deburring an ultrasonic surgical blade in accordance with the present invention.

FIGS. 13 and 14 illustrate a method of deburring the edges, including cutting-edges 36, of treatment region 26. Burrs are fragments of material at the blade 31 edges due to the manufacturing process. These burrs can cause inconsistent cutting speed from blade to blade resulting in a lowered sense of precision by the surgeon during use. It is desirable to remove the burrs to provide consistent function from blade to blade. However, standard deburring methods are less than optimal for preserving the advantages of cutting-surface 52 on edge 36.

Normally burrs are removed by, for example, buffing, sanding, or chemical etching. However standard deburring methods may dull edge 36 and decrease the cutting speed of blade 31. A novel approach to deburring ultrasonic devices such as blade 31 is to use the tuned ultrasonic properties of the ultrasonic surgical instrument 10 to deburr, as described below in conjunction with FIGS. 13 and 14.

In FIG. 13, ultrasonic transmission assembly 11 is shown acoustically coupled to hand-piece 56. Hand-piece 56 is electrically connected to generator 60, which is activated by foot-switch 58. Depressing foot-switch 58 activates generator 60, and delivers electrical energy to hand-piece 56. Hand-piece 56 converts the electrical energy to ultrasonic motion of ultrasonic transmission assembly 11 and treatment region 26. Treatment region 26 vibrates at an excursion magnitude of 20 micrometers to 150 micrometers, and at a frequency of approximately 55.5 kilohertz.

The method of deburring ultrasonically activated devices is illustrated in FIG. 14 using, as an example, treatment region 26 of the distal portion of ultrasonic surgical instrument 10. A jar 64, including a lid 66, contains an abrasive material, or media 62. Lid 66 includes at least one opening 68, through which treatment region 26 is inserted into media 62. Activation of treatment region 26 in media 62 deburrs treatment region 26 while maintaining desirable qualities of treatment region 26.

Media 62 is an abrasive material. For example, media 62 may include, either singly or in combinations, talc, crushed walnut shells, crushed fired ceramics, glass beads, plastic, Aluminum oxide, steel, sand, crushed champagne bottle glass, or other known materials used for polishing, bead-blasting, sand-blasting, or the like. For an ultrasonic surgical instrument such as treatment region 26, it is preferable to use crushed champagne bottle glass using particles of glass having a mesh size of from 10 to 40 mesh, and most preferably 24 mesh. A mesh is a size of screen or of particles passed by it in terms of the number of openings per linear inch. A suitable media is Aluma Glass #24, available from N. T. Ruddock, 26123 Broadway Ave., Cleveland, Ohio 44140.

Finer mesh media 62 produces a sand-blasted appearance without removing large burrs from treatment region 26. Coarser mesh media 62 removes large burrs from treatment region 26 and produces an appealing finish without dulling the cutting-edges 36 and compromising clinical efficacy. However, very course media does not remove burrs and leaves the blade 31 with a scratched or damaged surface appearance.

Short durations of blade 31 activation in media 62 knocks off large burrs, while maintaining cutting-edge 36 sharpness due to the motion of cutting-edges 36 preferred direction while in contact with media 62. Two to twenty seconds of activation are sufficient to remove all unwanted burrs without compromising sharpness, depending on media type and mesh size. Longer durations of activation will controllably decrease cutting-edge 36 radius, or sharpness, to optimize desired treatment region 26 efficacy.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. An ultrasonic surgical blade comprising:
   a flat bottom surface;
   a top surface, wherein said top surface has a width greater than said bottom surface; and
   a cutting-edge, wherein said cutting-edge is defined by a first cutting-surface intermediate said top surface and said bottom surface.

2. An ultrasonic surgical blade according to claim 1 wherein said ultrasonic surgical blade is sterile.

3. An ultrasonic surgical blade according to claim 1 wherein the included angle at the intersection between said top surface and said first cutting-surface is from about 25 to about 35 degrees.

4. An ultrasonic surgical blade according to claim 1, wherein said first cutting surface is curvilinear.

5. An ultrasonic surgical blade according to claim 1 wherein said top surface further comprises a second cutting-surface intersecting said first cutting-surface at said cutting-edge.

6. An ultrasonic surgical blade according to claim 5, wherein the intersection of said first cutting-surface and said second cutting-surface has an included angle of between about 10 to about 60 degrees.

7. An ultrasonic surgical blade according to claim 6, wherein the included angle between said first cutting-surface and said second cutting-surface is from about 25 to about 35 degrees.

8. An ultrasonic surgical blade according to claim 7, wherein at least a portion of said top surface is flat, and at least a portion of said first cutting-surface is flat, wherein said flat portion of said top surface is substantially parallel to said flat portion of said first cutting-surface.

9. An ultrasonic surgical blade according to claim 7 wherein said top surface has a width about 0.002 inches to about 0.060 inches wider than the width of said bottom surface.

10. An ultrasonic surgical blade according to claim 9 wherein said cutting-edge is sharp.

11. An ultrasonic surgical blade according to claim 9 wherein said cutting-edge is blunt.

12. An ultrasonic surgical blade according to claim 11 wherein said blunt cutting-edge is square.

13. The ultrasonic surgical blade of claim 1, wherein the blade is curved.

14. A curved ultrasonic surgical blade comprising:
a bottom surface;
a top surface;
a cutting-edge, wherein said cutting-edge is defined by a first cutting-surface intermediate said top surface and said bottom surface; and
said top surface comprising a second cutting-surface intersecting said first cutting-surface at said cutting edge.

15. A curved ultrasonic surgical blade according to claim 14, wherein the intersection of said first cutting-surface and said second cutting-surface has an included angle of between about 10 to about 60 degrees.

16. A curved ultrasonic surgical blade according to claim 15, wherein the included angle between said first cutting-surface and said second cutting-surface is from about 25 to about 35 degrees.

17. A curved ultrasonic surgical blade according to claim 16 wherein said top surface has a width about 0.002 inches to about 0.060 inches wider than the width of said bottom surface.

18. A curved ultrasonic surgical blade according to claim 17, wherein said first cutting-surface is curvilinear.

19. A curved ultrasonic surgical blade according to claim 17 wherein said cutting-edge is sharp.

20. A curved ultrasonic surgical blade according to claim 17 wherein said cutting-edge is blunt.

21. A curved ultrasonic surgical blade according to claim 17 wherein said curved ultrasonic blade is sterile.

22. A curved ultrasonic surgical blade according to claim 20 wherein said blunt cutting-edge is square.

23. A curved ultrasonic surgical blade according to claim 21, wherein at least a portion of said top surface is flat, and at least a portion of said first cutting-surface is flat, wherein said flat portion of said top surface is substantially parallel to said flat portion of said first cutting-surface.

24. The curved ultrasonic surgical blade according to claim 14, wherein the top surface has a width greater than the bottom surface.

* * * * *